(12) United States Patent
Kim et al.

(10) Patent No.: US 10,188,594 B2
(45) Date of Patent: Jan. 29, 2019

(54) FERMENTED VEGETABLE OILS AND METHODS OF PREPARING THE SAME

(71) Applicants: Korea Research Institute of Bioscience and Biotechnology, Daejeon (KR); Damy Chemical Co., Ltd., Seoul (KR)

(72) Inventors: Kwang-Nyeon Kim, Yongin-si (KR); Ju-Hyun Son, Bucheon-Shi (KR); Hee-Sik Kim, Daejeon (KR); Jong-Seok Yun, Anyang-si (KR)

(73) Assignees: DAMY CHEMICAL CO., LTD., Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/148,166

(22) Filed: May 6, 2016

(65) Prior Publication Data
US 2016/0354301 A1    Dec. 8, 2016

Related U.S. Application Data

(62) Division of application No. 14/241,137, filed as application No. PCT/KR2012/006801 on Aug. 24, 2012, now abandoned.

(30) Foreign Application Priority Data

Aug. 26, 2011 (KR) .................. 10-2011-0086094

(51) Int. Cl.
C12P 7/64      (2006.01)
A61K 8/92      (2006.01)
(Continued)

(52) U.S. Cl.
CPC .............. *A61K 8/922* (2013.01); *A23D 9/04* (2013.01); *A61K 8/361* (2013.01); *A61Q 19/00* (2013.01);
(Continued)

(58) Field of Classification Search
None
See application file for complete search history.

(56) References Cited

U.S. PATENT DOCUMENTS 8,226,965 B2 *   7/2012   Baker, Jr. ............. A61K 9/0014
                                                              424/400
8,529,886 B2     9/2013   Apt et al.
(Continued)

FOREIGN PATENT DOCUMENTS

JP   2004254595      9/2004
JP   2007-185142 A   7/2007
(Continued)

OTHER PUBLICATIONS

Kitamoto et al.(I),Agric. Biol. Chem., 54 ( 1), 31-36, 1990.*
(Continued)

*Primary Examiner* — Irene Marx
(74) *Attorney, Agent, or Firm* — Blank Rome LLP

(57) ABSTRACT

The present invention relates to a fermented vegetable oil, to a method for preparing the oil, and to a composition including the oil. More particularly, the present invention relates to a technique for providing a fermented vegetable oil having the effects of enhancing emulsion stability due to water retention ability, improving texture and flavor, and enhancing moisturization.

18 Claims, 13 Drawing Sheets

(51) Int. Cl.
*A61Q 19/00* (2006.01)
*A61K 8/36* (2006.01)
*A61Q 19/08* (2006.01)
*A23D 9/04* (2006.01)

(52) U.S. Cl.
CPC ............... *A61Q 19/08* (2013.01); *C12P 7/64* (2013.01); *C12P 7/6409* (2013.01); *C12P 7/6427* (2013.01); *C12P 7/6436* (2013.01); *A61K 2800/85* (2013.01)

(56) References Cited

U.S. PATENT DOCUMENTS

| 2010/0004472 A1 | 1/2010 | Kitagawa et al. |
| 2010/0255133 A1 | 10/2010 | Yagyu |
| 2011/0257116 A1 | 10/2011 | Kitagawa et al. |

FOREIGN PATENT DOCUMENTS

| JP | 2007-252279 A | 10/2007 |
| JP | 2009126820 A | 6/2009 |
| JP | 2009149566 | 7/2009 |
| JP | 2009149567 | 7/2009 |
| JP | 2010282614 | 12/2010 |
| JP | 05-091889 B2 | 12/2012 |
| WO | WO-2004/020647 A1 | 3/2004 |
| WO | WO-2007060956 A1 | 5/2007 |
| WO | WO-2008018448 A1 | 2/2008 |

OTHER PUBLICATIONS

Kitamoto et al., (II), Agric. Biol. Chem., 54 (1) 37-40, 1990.*
Morita et al., FEMS Yeast Res. vol. 7 (2007) pp. 286-292.*
Adamczak et al,. Biotechnology Letters 22: 313-316, 2000.*
Kamai et al., JP 200454595, Sep. 16, 2004, machine translation.*
Kim et al., Biotechnology Letters 24: 225-229, 2002.*
Patrick et al., JAOCS, vol. 74, No. 3 (1997), pp. 273-276.*
Fukuoka et al., "Characterization of new types of mannosylerythritol lipids as biosurfactants produced from soybean oil by a basidiomycetous yeast, *Pseudozyma shanxiensis*," J. Oleo Sci., 2007, 56(8), pp. 435-442.
Kim et al., "Extracellular production of a glycolipid biosurfactant, mannosylerythritol lipid, by *Candida* sp. SY16 using fed-batch fermentation," Appl. Microbiol. Biotechnol., 2006, 70(4), pp. 391-396.
Morita et al., "Efficient production of Di- and Tri-acylated mannosylerythritol lipids as glycolipid biosurfactants by pseudozyma parantarctica JCM 11752," J. Oleo Sci., 2008, 57(10), pp. 557-565.
Morita et al., FEMS Yeast Res. Mar. 2007; 7(2):286-92.
Chabiri et al., 2009. "Comarative Quality Assessment of Branded and Unbranded Edible Vegetable Oils in Nigeria". Pacific Journal of Science Technology. 10(2):927-934.

\* cited by examiner

Olive Oil

Fermented Olive Oil

Linoleic acid

Linolenic acid

Fermented Olive Oil

Soy Bean Oil

Fermented Soy Bean Oil

Green Tea Oil

Fermented Green Tea Oil

Argan Oil

Fermented Argan Oil

FERMENTED VEGETABLE OILS AND METHODS OF PREPARING THE SAME

FIELD OF THE INVENTION

The present invention relates to a fermented vegetable oil and a composition including same, and more particularly, and provides a fermented vegetable oil, which has the effects of enhancing emulsion stability due to water retention ability, improving texture and flavor and enhancing moisturization, according to being fermented by yeast.

BACKGROUND OF THE INVENTION

Developing various techniques, which can induce functional change by changing oil composition, is very important to meet industrial needs for developing various products.

In general, a fermented oil refers to an oil, which is prepared by fermenting oriental medicine such as ginseng, extracting fat-soluble ingredients therefrom and adding thereof to an oil, or which is prepared by adding oriental medicine such as ginseng to an oil followed by maturing thereof.

Further, an oil, which is prepared by fermenting fishes or coconut and extracting fat-soluble ingredients therefrom, or an oil, which is prepared by soaking germinating or steaming oil seeds (soy bean, sun flower seed, grape seed, sesame seed and the like) and then extracting an oil therefrom, is also called a fermented oil.

However, there is no technique, which improves structure, function and flavor by culturing yeast in a large amount of oil and fermenting thereof.

SUMMARY OF THE INVENTION

The present invention provides a fermented vegetable oil, which has the effects of enhancing emulsion stability due to water retention ability, improving texture and flavor, and enhancing moisturizing capacity, according to being fermented by yeast.

Further, the present invention provides a method for preparing a fermented vegetable oil, which is fermented by yeast by a simple method.

Further, the present invention provides a composition for skin external preparations or cosmetics, which has the effect of enhancing emulsion stability, improving texture and flavor, and enhancing moisturizing capacity, by containing a fermented vegetable oil fermented by yeast as an active ingredient.

In order to accomplish one object of the present invention, the fermented vegetable oil of the present invention is characterized by being fermented by yeast.

In order to accomplish another object of the present invention, the method for preparing the fermented vegetable oil of the present invention is characterized by comprising: (a) a step of firstly culturing yeast in a culture solution at an aerobic condition; (b) a step of secondarily culturing after adding a vegetable oil to the culture solution; and (c) a step of collecting the secondarily cultured vegetable oil.

In order to accomplish further another object of the present invention, the composition for skin external preparations or cosmetics of the present invention is characterized by comprising the fermented vegetable oil, which is fermented by yeast, as an active ingredient.

ADVANTAGEOUS EFFECTS OF THE INVENTION

The fermented vegetable oil according to the present invention is excellent on emulsion stability due to water retention ability. Accordingly, it is easy to manufacture a toner or essence-type products by applying the oil thereto.

Further, the fermented vegetable oil according to the present invention has lighter texture and more excellent moisture feeling than before fermentation.

Further, the fermented vegetable oil according to the present invention has higher stability and usability than a natural oil and a matured oil having similar effects.

BRIEF DESCRIPTION OF DRAWINGS

FIGS. 1A-M: the analysis result of the emulsion stability, wherein FIG. 1A is the result of measuring the emulsion activity of an olive oil, FIG. 1B is an image of estimating the emulsion stability of an olive oil depending on time, FIG. 1C is the result of measuring the emulsion activity of a fermented olive oil, FIG. 1D is an image of estimating the emulsion stability of a fermented olive oil depending on time, FIG. 1E is the result of comparing the emulsion activities of fermented oils depending on type, FIGS. 1F and 1G illustrate soy bean oil before and after fermentation, respectively; FIGS. 1H and 1I illustrate olive oil before and after fermentation, respectively; FIGS. 1J and 1K illustrate green tea oil before and after fermentation, respectively; and FIGS. 1L and 1M illustrate argan oil before and after fermentation, respectively.

FIGS. 2A-2C illustrate the result of analyzing fatty acid by gas chromatography, wherein FIG. 2A is a fatty acid distribution chart, FIG. 2B is the result of analyzing fatty acid of an olive oil, and FIG. 2C is the result of analyzing fatty acid of a fermented olive oil.

FIGS. 3A-B illustrate the result of measuring the acid value, wherein FIG. 3A is the result of measuring the acid value of an olive oil, and FIG. 3B is the result of measuring the acid value of a fermented olive oil.

FIGS. 4A-D illustrate the result of measuring the influence on the cell growth and toxicity in human fibroblasts, wherein FIG. 4A is the result of the cell viability of a soy bean oil and a fermented soy bean oil, FIG. 4B is the result of the cell viability of an olive oil and a fermented olive oil, FIG. 4C is the result of the cell viability of a green tea oil and a fermented green tea oil, and FIG. 4D is the result of the cell viability of an argan oil and a fermented argan oil.

FIGS. 5A-K illustrate the result of analyzing ingredients by using TLC (Thin layer chromatography), wherein FIG. 5A is the result of 2D-TLC of an olive oil, FIG. 5B is the result of 2D-TLC of a fermented olive oil, FIG. 5C is the result of 2D-TLC of a linoleic acid, FIG. 5D is the result of 2D-TLC of a linolenic acid, FIG. 5E is the result of 2D-TLC of a fermented olive oil, FIG. 5F is the result of 2D-TLC of a soy bean oil, FIG. 5G is the result of 2D-TLC of a fermented soy bean oil, FIG. 5H is the result of 2D-TLC of a green tea oil, FIG. 5I is the result of 2D-TLC of a fermented green tea oil, FIG. 5J is the result of 2D-TLC of an argan oil, and FIG. 5K is the result of 2D-TLC of a fermented argan oil.

DETAILED DESCRIPTION OF THE INVENTION

Figure 1A:
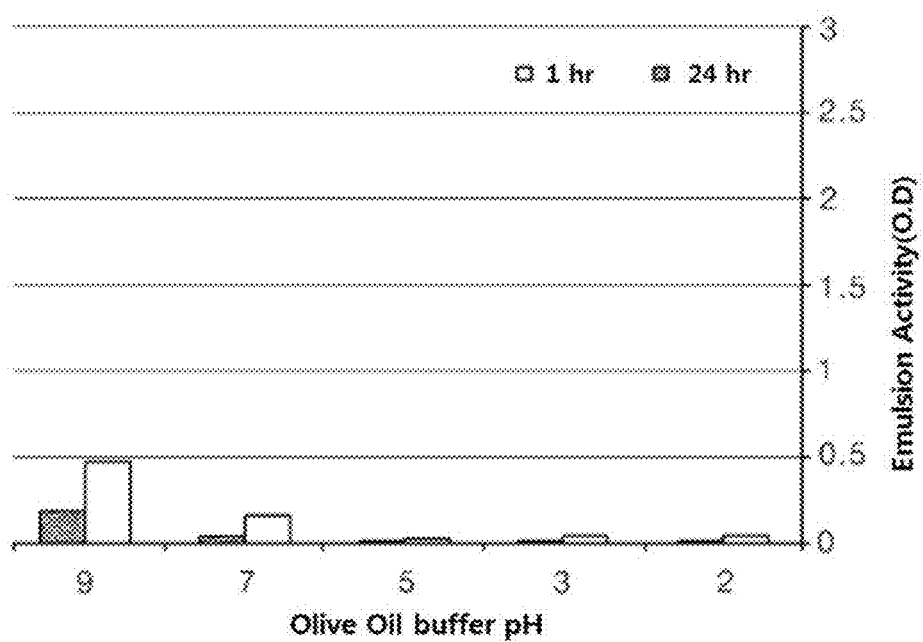
Figure 1B:
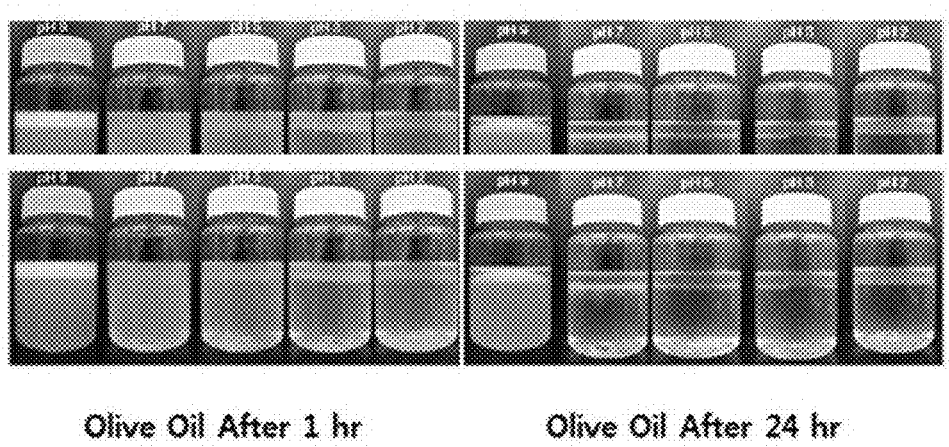
Figure 1C:
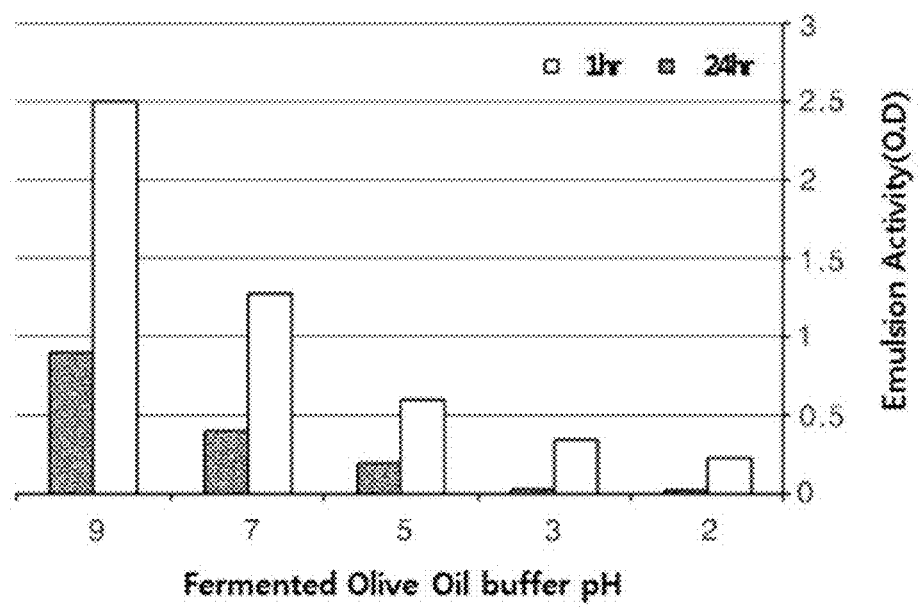
Figure 1D:
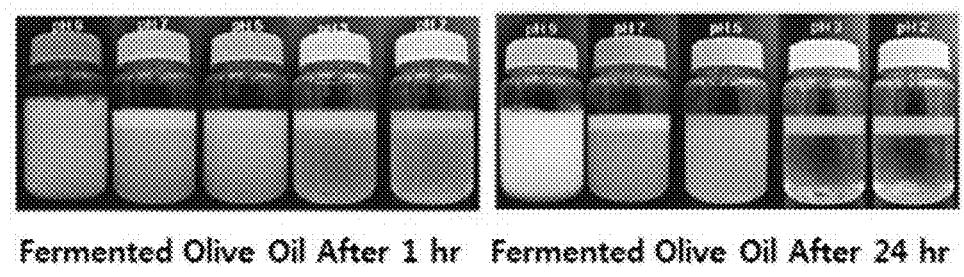

The above and other aspects, features, and advantages of the invention will become apparent from the detailed description of the following embodiments in conjunction with the accompanying drawings. It should be understood that the present invention is not limited to the following embodiments and may be embodied in different ways, and that the embodiments are provided for complete disclosure and a thorough understanding of the invention to those skilled in the art.

Hereinafter, the fermented vegetable oil, the method for preparing the same, and the composition including the same according to exemplary embodiments of the present invention will be described in detail with reference to the accompanying drawings.

Fermented Vegetable Oil

The fermented vegetable oil of the present invention is characterized by being fermented by yeast.

Herein, the yeast may be SY16 (KCTC 8950P) of *Pseudozyma* sp., preferably, and the SY16 (KCTC 8950P) of *Pseudozyma* sp. is in the shape of cylinder and grows in polar germination mode, and forms endospores, which differ from hyphae and ascospores. Pursuant to the Budapest Treaty, a deposit of SY16 of *Pseudozyma* sp. yeast was made at the Korean Collection for Type Cultures, at the Korea Research Institute of Bioscience and Biotechnology, on Jun. 18, 1999 under accession number KCTC 8950P.

Further, the fermented vegetable oil of the present invention is characterized that it is fermented by the above yeast in a medium containing a vegetable oil having the acid value of 0.100~2.000.

Herein, the vegetable oil fermented in the medium may be any general vegetable oil such as olive oil, soy bean oil, green tea oil and argan oil, and it may be an oil having the acid value of 0.100~2.000, preferably. In particular, because the lower acid value makes the higher fermentation efficiency, the acid value is preferred to be 0.1~0.5. There is very little vegetable oil having the acid value of less than 0.100, and the fermentation efficiency may be reduced if the acid value is over 2.000.

The fermented vegetable oil of the present invention is characterized by having higher essential fatty acid content than before fermentation, by being fermented by the yeast. At this time, the essential fatty acid content after fermentation is 5.0~140.0 times higher than before fermentation.

Herein, the essential fatty acid is preferred to be linoleic acid. The linoleic acid is a key component of the epidermal lipid bilayer, and is contained in ceramides of the epidermal keratin layer. This linoleic acid is effective in skin moisturizing, skin homeostasis maintenance, formation and protection of the skin permeation layer. Accordingly, the essential fatty acid contained in the fermented vegetable oil of the present invention may be linoleic acid, preferably.

Further, the fermented vegetable oil of the present invention is characterized by having higher free fatty acid content than before fermentation, by being fermented by the yeast. At this time, the free fatty acid content after fermentation is 5.0~140.0 times higher than before fermentation.

Herein, the free fatty acid refers to fatty acid that is in unbound glyceride form. When the free fatty acid content becomes higher, texture becomes improved because stickiness is reduced, and it is effective in enhancing oiliness after use. Accordingly, it is preferred that the fermented vegetable oil of the present invention has higher free fatty acid content.

Method for Preparing Fermented Vegetable Oil

The method for preparing the fermented vegetable oil of the present invention includes (a) a step of firstly culturing yeast in a culture solution at an aerobic condition; (b) a step of secondarily culturing after adding a vegetable oil to the culture solution; and (c) a step of collecting the secondarily cultured vegetable oil.

First of all, (a) yeast are firstly cultured in a culture solution at an aerobic condition.

Herein, the yeast may be SY16 (KCTC 8950P) of *Pseudozyma* sp., preferably. The SY16 (KCTC 8950P) of *Pseudozyma* sp. is in the shape of cylinder and grows in polar germination mode, and forms endospores, which differ from hyphae and ascospores.

Herein, the culture solution does not contain a vegetable oil yet, and it is very important to mix various kinds of culture materials to make the vegetable oil be fermented well. In particular, it is preferred to use at least one selected from the group consisting of glucose, yeast extract, malt extract, peptone, soya bean meal, $(NH_4)_2SO_4$, $KH_2PO_4$, $MgSO_4$, $CaCl_2$ and NaCl.

The first culture time may be 24~72 hours, and 30~60 hours, preferably because the lipase activity is the highest within the said range.

Then, (b) a vegetable oil is added to the firstly cultured solution and then the resulting solution is secondarily cultured.

In order to optimize the fermentation of the vegetable oil in the culture solution, it is preferred to use a vegetable oil having lower acid value. Namely, the optimized culture condition is determined by the acid value of a vegetable oil. Accordingly, the acid value of a vegetable oil may be in the range of 0.10~02.000, preferably, and it may be in the range of 0.1~0.5, more preferably, because the lower acid value makes the higher fermentation efficiency. There is very little vegetable oil having the acid value of less than 0.100, and the fermentation efficiency may be reduced if the acid value is over 2.000.

Herein, the vegetable oil is added in an amount of 100 parts by weight or less, based on 100 parts by weight of the above culture solution, in which the vegetable oil is not added yet. The amount of the vegetable oil added may be properly adjusted according to the desired amount of a fermented vegetable oil, but when the vegetable oil is added in an amount of over 100 parts by weight, based on the 100 parts by weight of the culture solution containing the vegetable oil, it is worried that the oil may not be fermented enough.

Herein, the second culture time may be 72~120 hours, preferably because the time enough to produce the maximum amount of free fatty acid should be secured as the fermentation, resulting from the secondary culture, goes on. Further, the time may vary depending on the kinds of vegetable oils. Accordingly, the secondary culture may be finished when the amount of the free fatty acid is not increased any more after measuring the amount of the free fatty acid increased with time.

Finally, (c) the secondarily cultured vegetable oil is collected.

There is no limit to the method for collecting. The collected vegetable oil is a fermented oil, and it can be used as an active ingredient of a composition for skin external preparations or cosmetics.

Composition for Skin External Preparations or Cosmetics Containing Fermented Vegetable Oil as Active Ingredient The present invention includes a composition, which contains the fermented vegetable oil fermented by yeast, as an active ingredient, and is used for skin external preparations or cosmetics.

The inventive fermented vegetable oil, which is fermented by yeast, is suitable for a composition for skin external preparations or cosmetics because it has excellent texture and moisturizing capacity due to its high emulsion activity and emulsion stability, and much higher contents of essential fatty acid and free fatty acid than general oils.

At this time, the amount of the fermented vegetable oil contained in the composition for skin external preparations and cosmetics may be 2~40 wt %, preferably.

If the amount of the fermented vegetable oil is less than 2 wt %, the effect of the product may be meager because the fermented vegetable oil is not contained enough, and if the amount is over 40 wt %, it may be difficult to be formulated.

Ingredients contained in the composition for skin external preparations and cosmetics of the present invention may contain general ingredients used for compositions for skin external preparations and cosmetics in addition to the said fermented vegetable oil, for example, general additives such as antioxidant, stabilizer, solubilizer, vitamin, dye and fragrance, and carriers.

The composition for skin external preparations and cosmetics of the present invention may be formulated in a wide variety of forms commonly used in the art, for example, solution, suspension, emulsion, paste, gel, cream, lotion, powder, soap, surfactant-containing cleanser, oil, powder foundation, emulsion foundation, wax foundation and spray, but not limited thereto.

The carrier contained in the present composition for skin external preparations and cosmetics may be any carrier commonly used in the art depending on the type of the formulation.

In the formulation of ointment, paste, cream or gel, the carrier ingredient may be animal and vegetable fats, wax, paraffin, starch, tragacanth, cellulose derivatives, polyethylene glycol, silicone, bentonite, silica, talc, zinc oxide and the like.

In the formulation of powder or spray, the carrier ingredient may be lactose, talc, silica, aluminum hydroxide, calcium silicate or polyamide powder. In particular, the spray may further comprise propellants such as chlorofluorohydrocarbon, propane/butane or dimethyl ether.

In the formulation of solution and emulsion, the carrier ingredient may be solvent, solubilizer and emulsifier. For example, it may be water, ethanol, isopropanol, ethyl carbonate, ethyl acetate, benzyl alcohol, benzyl benzoate, propylene glycol, 1,3-butylglycol oil, in particular, cottonseed oil, peanut oil, maize germ oil, olive oil, castor oil and sesame seed oil, glycerol fatty esters, polyethylene glycol and fatty acid esters of sorbitan.

In the formulation of suspension, the carrier ingredient may be liquid diluents, for example, water, ethanol or propylene glycol, suspending agents, for example, ethoxylated isosteary alcohol, polyoxyethylene sorbitol ester and poly oxyethylene sorbitan ester, micocrystalline cellulose, aluminum metahydroxide, bentonite, agar or tragacanth.

In the formulation of a surfactant-containing cleanser, the carrier ingredient may be aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamidobetaine, aliphatic alcohol, fatty acid glycerides, fatty acid diethanolamide, vegetable oils, lanolin derivatives or ethoxylated glycerol fatty acid ester.

In the formulation of soap, the carrier ingredient may be alkali metal salts of fatty acids, salts of fatty acid hemiesters, fatty acid protein hydrolysates, isethionate, lanolin derivatives, aliphatic alcohol, vegetable oil, glycerol, sugars and the like.

Moreover, the cosmetic composition of the present invention may include other additives in addition to the carrier, for example, preservative, antioxidant, stabilizer, solubilizer, vitamin, dye and fragrance.

EXAMPLE

<Optimum Medium Composition for Fermented Oil Production by Yeast>

In order to determine medium composition suitable for fermented oil production by yeast, SY16 [KCTC 8950P] of *Pseudozyma* sp. was inoculated to each 1 L of the following 8 medium compositions, and cultured at 25° C., 300 rpm, under an aerobic condition.

TABLE 1

| Medium composition for fermented oil production by yeast oil | | | |
|---|---|---|---|
| Composition 1 | Composition 2 | Composition 3 | Composition 4 |
| Glucose 15 g/L<br>Olive oil 100 g/L<br>$(NH_4)_2SO_4$ 1 g/L<br>$K_2HPO_4$ 2.5 g/L<br>$MgSO_4$ 0.5 g/L<br>$CaCl_2$ 0.1 g/L<br>$MnSO_4$ 0.02 g/L<br>$NaH_2PO_4$ 0.1 g/L<br>Peptone 1 g/L<br>Distilled water 879.78 g/L | Sucrose 10 g/L<br>Olive oil 100 g/L<br>Yeast extract 3 g/L<br>Skim milk 3 g/L<br>Casein 3 g/L<br>Soya bean meal 3 g/L<br>$NH_4NO_3$ 2 g/L<br>$KH_2PO_4$ 1 g/L<br>$MgSO_4$ 0.5 g/L<br>$CaCl_2$ 0.1 g/L<br>NaCl 0.1 g/L<br>Distilled water 874.3 g/L | Glucose 10 g/L<br>Olive oil 100 g/L<br>Yeast extract 3 g/L<br>Malt extract 3 g/L<br>Peptone 5 g/L<br>Distilled water 879 g/L | Glucose 10 g/L<br>Olive oil 100 g/L<br>Yeast extract 3 g/L<br>Malt extract 3 g/L<br>Peptone 3 g/L<br>Soya bean meal 3 g/L<br>$(NH_4)_2SO_4$ 2 g/L<br>$KH_2PO_4$ 1 g/L<br>$MgSO_4$ 0.5 g/L<br>$CaCl_2$ 0.1 g/L<br>NaCl 0.1 g/L<br>Distilled water 874.3 g/L |
| Composition 5 | Composition 6 | Composition 7 | Composition 8 |
| Glucose 10 g/L<br>Argan oil 100 g/L<br>Yeast extract 3 g/L<br>Malt extract 3 g/L<br>Peptone 3 g/L<br>Soya bean meal 3 g/L<br>$(NH_4)_2SO_4$ 2 g/L<br>$KH_2PO_4$ 1 g/L<br>$MgSO_4$ 0.5 g/L | Glucose 10 g/L<br>Green tea seed oil 100 g/L<br>Yeast extract 3 g/L<br>Malt extract 3 g/L<br>Peptone 3 g/L<br>Soya bean meal 3 g/L<br>$(NH_4)_2SO_4$ 2 g/L<br>$KH_2PO_4$ 1 g/L | Glucose 10 g/L<br>Grape seed oil 100 g/L<br>Yeast extract 3 g/L<br>Malt extract 3 g/L<br>Peptone 3 g/L<br>Soya bean meal 3 g/L<br>$(NH_4)_2SO_4$ 2 g/L<br>$KH_2PO_4$ 1 g/L | Glucose 10 g/L<br>Meadowfoam seed oil 100 g/L<br>Yeast extract 3 g/L<br>Malt extract 3 g/L<br>Peptone 3 g/L<br>Soya bean meal 3 g/L<br>$(NH_4)_2SO_4$ 2 g/L<br>$KH_2PO_4$ 1 g/L |

TABLE 1-continued

| Medium composition for fermented oil production by yeast oil | | | |
|---|---|---|---|
| CaCl$_2$ 0.1 g/L | MgSO$_4$ 0.5 g/L | MgSO$_4$ 0.5 g/L | MgSO$_4$ 0.5 g/L |
| NaCl 0.1 g/L | CaCl$_2$ 0.1 g/L | CaCl$_2$ 0.1 g/L | CaCl$_2$ 0.1 g/L |
| Distilled water 874.3 g/L | NaCl 0.1 g/L | NaCl 0.1 g/L | NaCl 0.1 g/L |
| | Distilled water 874.3 g/L | Distilled water 874.3 g/L | Distilled water 874.3 g/L |

After 24 hours, 1 ml of each culture solution was collected, and the growth and lipase activity of the yeast were measured by using a spectrophotometer.

The yeast1 growth was measured by culturing the yeast at each condition, centrifuging thereof to remove an oil layer, strongly mixing the resulting solution for 20 sec, diluting the mixed solution 10 times with distilled water, and then measuring absorbance (660 nm) of each sample.

In order to measure the lipase activity of the yeast, the culture solution was centrifuged at 12,000 rpm for 3 min, the supernatant was used as a crude enzyme solution, and then the lipase activity was measured by microplate analyzing method measuring the amount of p-nitrophenol (pNP) bound to a substrate, which is released by the said enzyme, as the change of absorbance (405 nm). As the result of measuring the growth and lipase activity of the yeast, the composition 4 showed the highest growth and lipase activity. Accordingly, the composition was used for preparing the next fermented oil. For the lipase activity, the amount that the crude enzyme 100 μL produces tyrosine 1 μg for 1 min was used as 1 unit.

As the result, the composition 4 showed the highest growth and lipase activity of the yeast. Accordingly, the composition 4 was determined as the optimum medium composition for the future fermented oil production by yeast.

TABLE 2

Yeast growth and lipase activity according to medium composition

| | Composition | | | | | | | |
|---|---|---|---|---|---|---|---|---|
| | 1 | 2 | 3 | 4 | 5 | 6 | 7 | 8 |
| Absorbance (O.D at 660 nm) | 1.006 | 0.841 | 1.237 | 1.803 | 1.103 | 1.552 | 1.391 | 1.669 |
| Lipase activity (U/mL) | 1.9 | 1.1 | 2.9 | 3.4 | 2.1 | 2.9 | 2.6 | 3.2 |

<Preparation of Fermented Oil by Yeast>

1. First Culture

SY16 [KCTC 8950P] of *Pseudozyma* sp. was inoculated to a culture solution (glucose 10 g/L, olive oil 100 g/L, yeast extract 3 g/L, malt extract 3 g/L, peptone 3 g/L, soya bean meal 3 g/L, (NH$_4$)$_2$SO$_4$ 2 g/L, KH$_2$PO$_4$ 1 g/L, MgSO$_4$ 0.5 g/L, CaCl$_2$ 0.1 g/L, NaCl 0.1 g/L: the medium of the composition 4) 1 L, and cultured at 25° C., 300 rpm under an aerobic condition.SY16 [KCTC 8950P] of *Pseudozyma* sp. was inoculated to a culture.

After culture, the culture solution 1 ml was collected at each time point (3, 7, 12, 24, 48, 72 and 96 hr), and then the growth and lipase activity of the yeast were measured at 660 nm by using a spectrophotometer. As the result of measuring the lipase activity, it was found that the first culture time showing the highest lipase activity was 48 hr.

2. Second Culture and Preparation of Fermented Oil

SY16 [KCTC 8950P] of *Pseudozyma* sp. was inoculated to the culture solution as described above 100 L, and cultured for 48 hours for conducting the first culture. Then, olive oil 100 L was added to the culture solution, and secondarily cultured at 25° C., 500 rpm under an aerobic condition. After the second culture, the culture solution 0.3~0.5 L was collected at each time point (3, 7, 12, 24, 48, 72, 96 and 120 hr), and then only oil part was collected. The degree of oil fermentation was checked by measuring the amount of free fatty acid in the collected oil. As the result of measuring the increased amount of the free fatty acid, the amount of the free fatty acid was the highest at the time of 96 hr after adding the oil, but the amount was not increased after that time.

<Test>

1. Emulsion Activity and Emulsion Stability

Emulsion stability means the ability of an emulsifier, which stabilizes emulsion after forming the emulsion or at the condition of mixing, high temperature, centrifugation and the like.

In order to measure the emulsion activity, each 1 ml of an olive oil and a fermented olive oil was dissolved in each 10 ml of buffer solutions depending on pH, and emulsified by completely stirring thereof for 2 min. Then, the resulting solution was kept for 10 min, and then the emulsion activity was measured by measuring absorbance at 620 nm. The emulsion stability was obtained as the percentage of the absorbance after 24 hrs to the initial absorbance. At pH 9.0, the absorbance was beyond the maximum absorbance value of the fermented oil, but the value set by a prediction program of the device was recorded.

The emulsion activities of the olive oil and the fermented olive oil depending on pH were listed in the following Table 2. As the result of the test, the emulsion activity of the fermented olive oil was rapidly increased from pH 5.0. In particular, it was confirmed that the emulsion activity at pH 9.0 was 50% or higher than at pH 5.0. On the other hand, the emulsion activity of the olive oil was increased at pH 9.0, but the emulsion activity at pH 9.0 was below the emulsion activity of the fermented olive oil at pH 5.0. As the result of comparing the emulsion activities of the fermented olive oil and the olive oil, the emulsion activity of the fermented olive oil was showed from pH 2.0, and it was confirmed that the emulsion activity of the fermented olive oil at pH 9.0 was 2.5 times or higher than that of the olive oil.

TABLE 3

Emulsification activity against pH of olive oil and fermented olive oil

| Buffer pH | Olive oil | Fermented olive oil |
|---|---|---|
| 2.0 | 0.400 | 0.820 |
| 3.0 | 0.428 | 0.972 |
| 5.0 | 0.520 | 2.633 |
| 7.0 | 0.514 | 2.800 |
| 9.0 | 1.602 | 4.215 |

The results about the emulsion stability were shown in FIG. 1. FIG. 1a is the result of measuring the emulsion activity of the olive oil, FIG. 1c is the result of measuring the emulsion activity of the fermented olive oil. Further, the emulsion stability of each sample was evaluated by taking images after 1 hr and 24 hrs. FIG. 1b is the image about the olive oil, and FIG. 1d is the image about the fermented olive oil.

After 24 hrs, the olive oil showed very little emulsion activity, but the fermented olive oil showed excellent emulsion activity as much as 4 times or more than the olive oil.

The emulsion activities of the various kinds of oils before and after fermentation were listed in the following Table 4.

TABLE 4

| Buffer pH 7.0 | Before fermentation (O.D) | After fermentation (O.D) |
|---|---|---|
| Soy bean oil | 0.514 | 2.746 |
| Olive oil | 0.517 | 2.800 |
| Green tea oil | 0.680 | 2.729 |
| Argan oil | 1.026 | 2.481 |

Figure 1E:
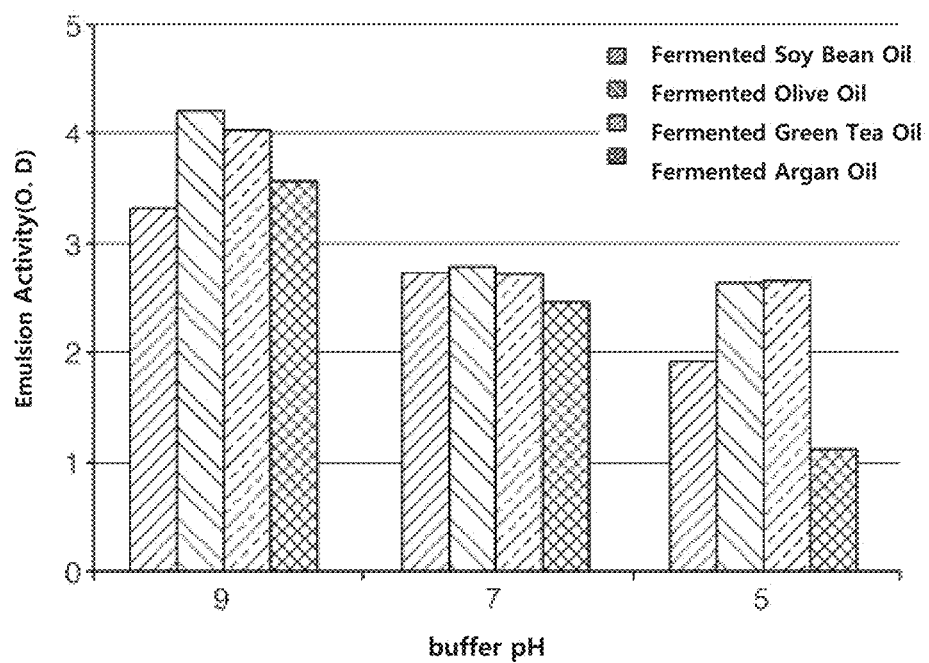
Figure 1F:
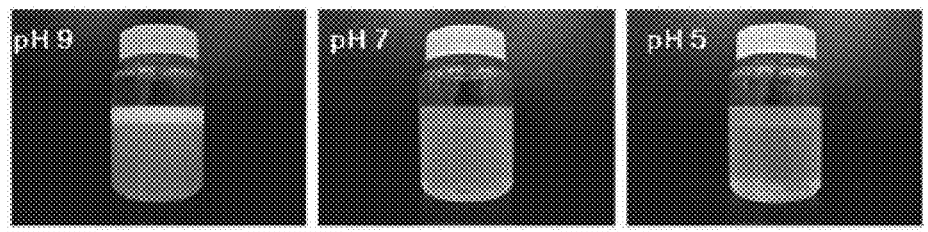
Figure 1G:
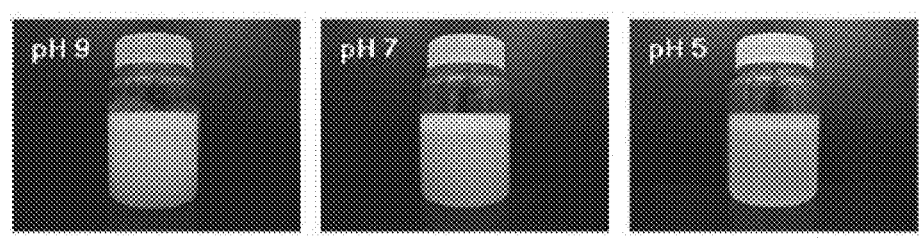
Figure 1H:
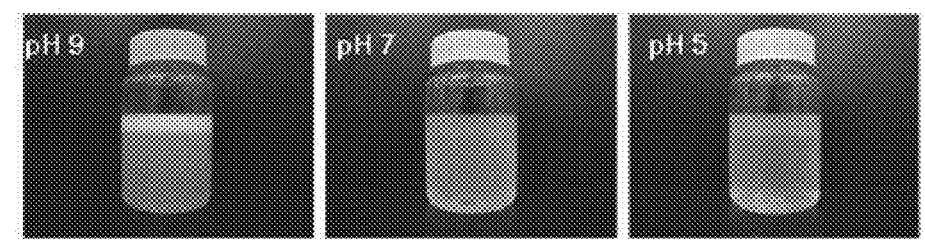
Figure 1I:
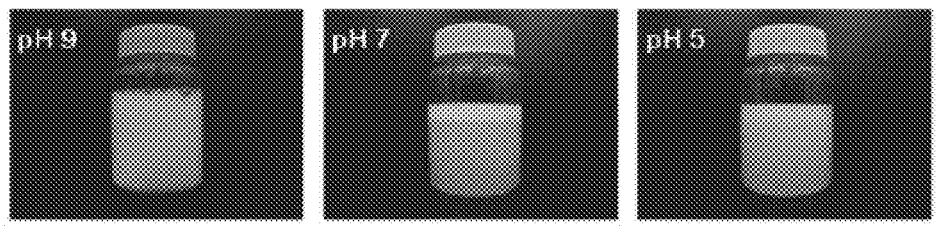
Figure 1J:
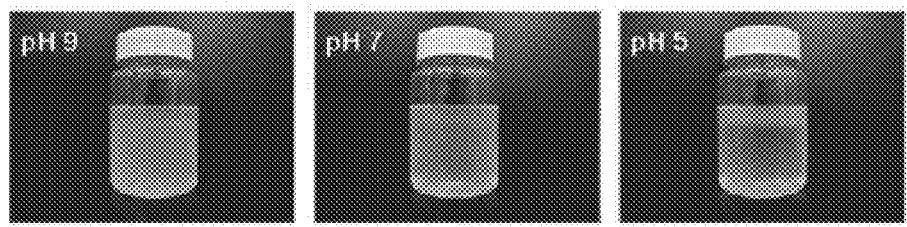
Figure 1K:
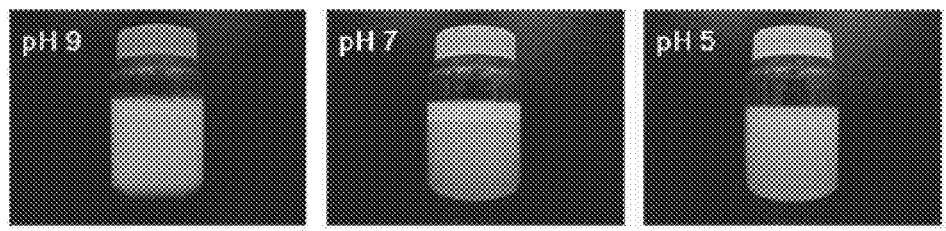
Figure 1L:
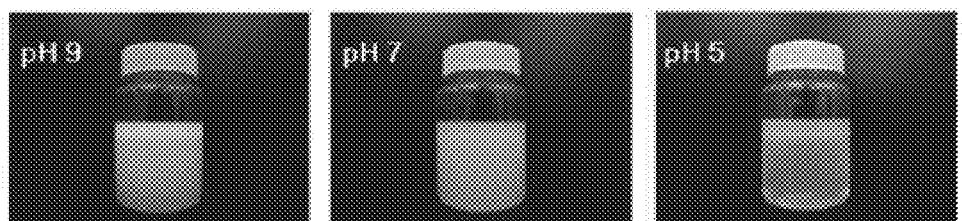
Figure 1M:
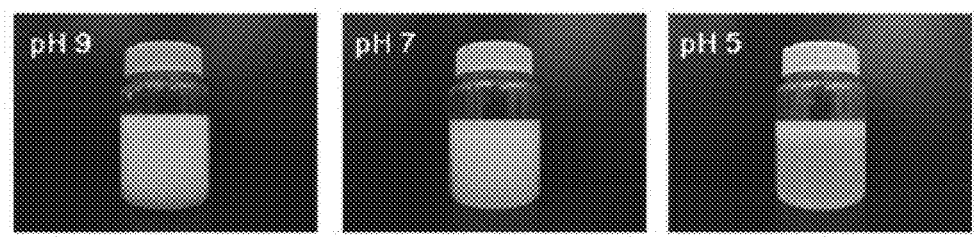

FIG. 1e is the result of measuring the emulsion activities of the fermented oils, and FIG. 1f to FIG. 1m are images about the emulsion activities.

As the result of the test, it was confirmed that the fermented oils have improved emulsifying capacity because they showed at least 2 times higher emulsion activities than before fermentation.

2. Texture

Per each test item about skin feeling (moisture, stickiness, oiliness and the like), 10 professional subjects were prepared, and texture against the olive oil and the fermented oil were evaluated. Evaluation was conducted according to the basic score of the following Table 5, and the scores of the subjects of each item were summed up and listed in the following Table 6.

TABLE 5

| Classification | Basic score |
|---|---|
| Very excellent | 5 |
| Excellent | 4 |
| Average | 3 |
| Poor | 2 |
| Very poor | 1 |

TABLE 6

| Classification | Olive oil | Fermented olive oil |
|---|---|---|
| Moisture feeling | 20 | 36 |
| Stickiness | 22 | 41 |
| Oiliness | 12 | 32 |

As the result of the test, the fermented olive oil had better moisture feeling, lower stickiness and not oiliness, compared with the olive oil. Accordingly, it could be found that the fermented oil of the present invention has excellent skin texture such as moisture feeling, stickiness, oiliness and the like.

3. Analysis of Fatty Acid Composition by Gas Chromatography (GC)

In order to check the change on the fatty acid composition in the olive oil through the fermentation process, the fatty acid was analyzed by gas chromatography (GC).

Fatty acid methyl ester was deacylated, the fatty acid, which can be dissolved in hexane, was prepared as boron trifluoride methanol mixture, and then, analyzed by GC analyzer (JMS-SX 102A, JEOL, Tokyo, Japan).

Figure 2A:
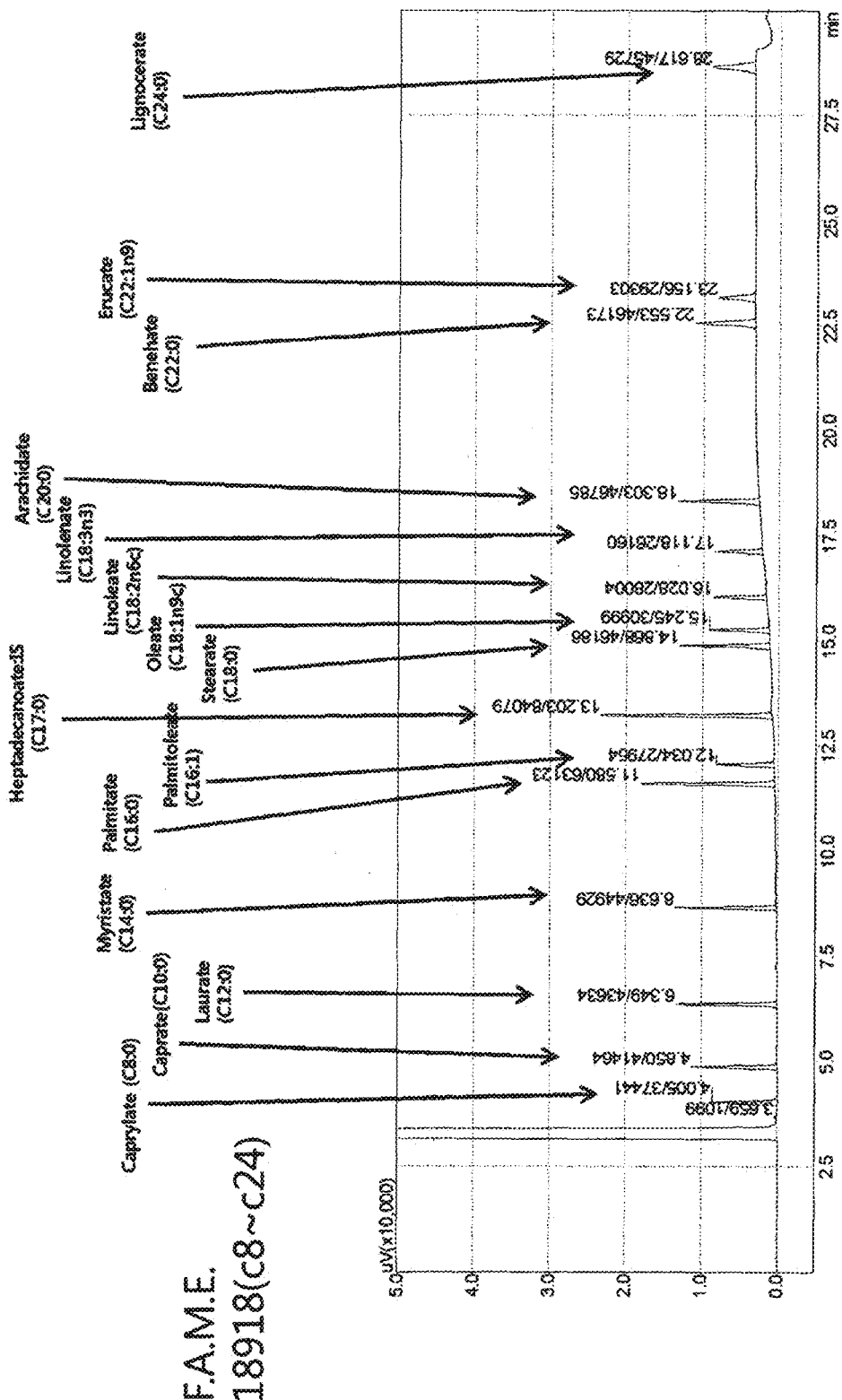
Figure 2B:
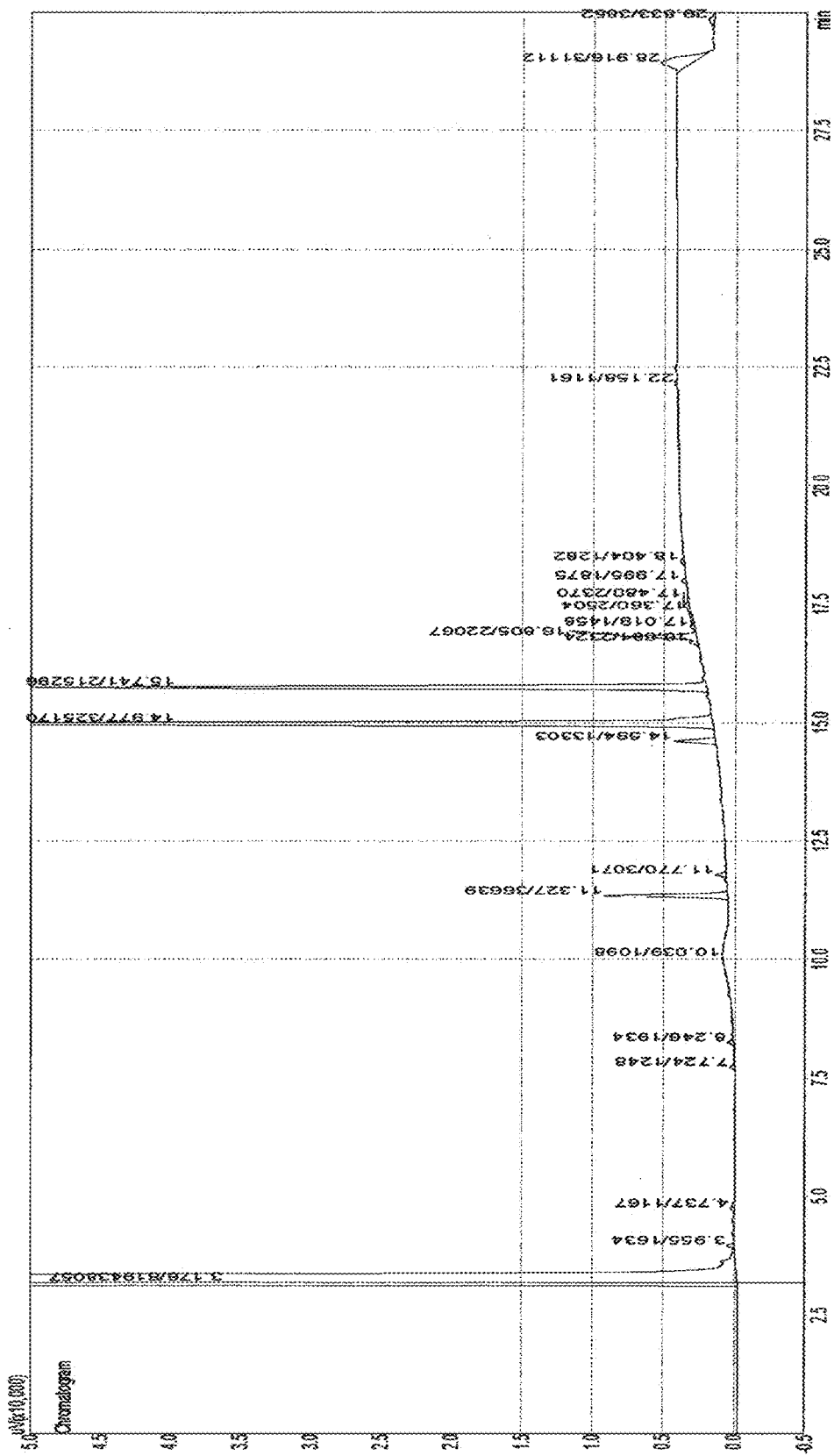
Figure 2C:
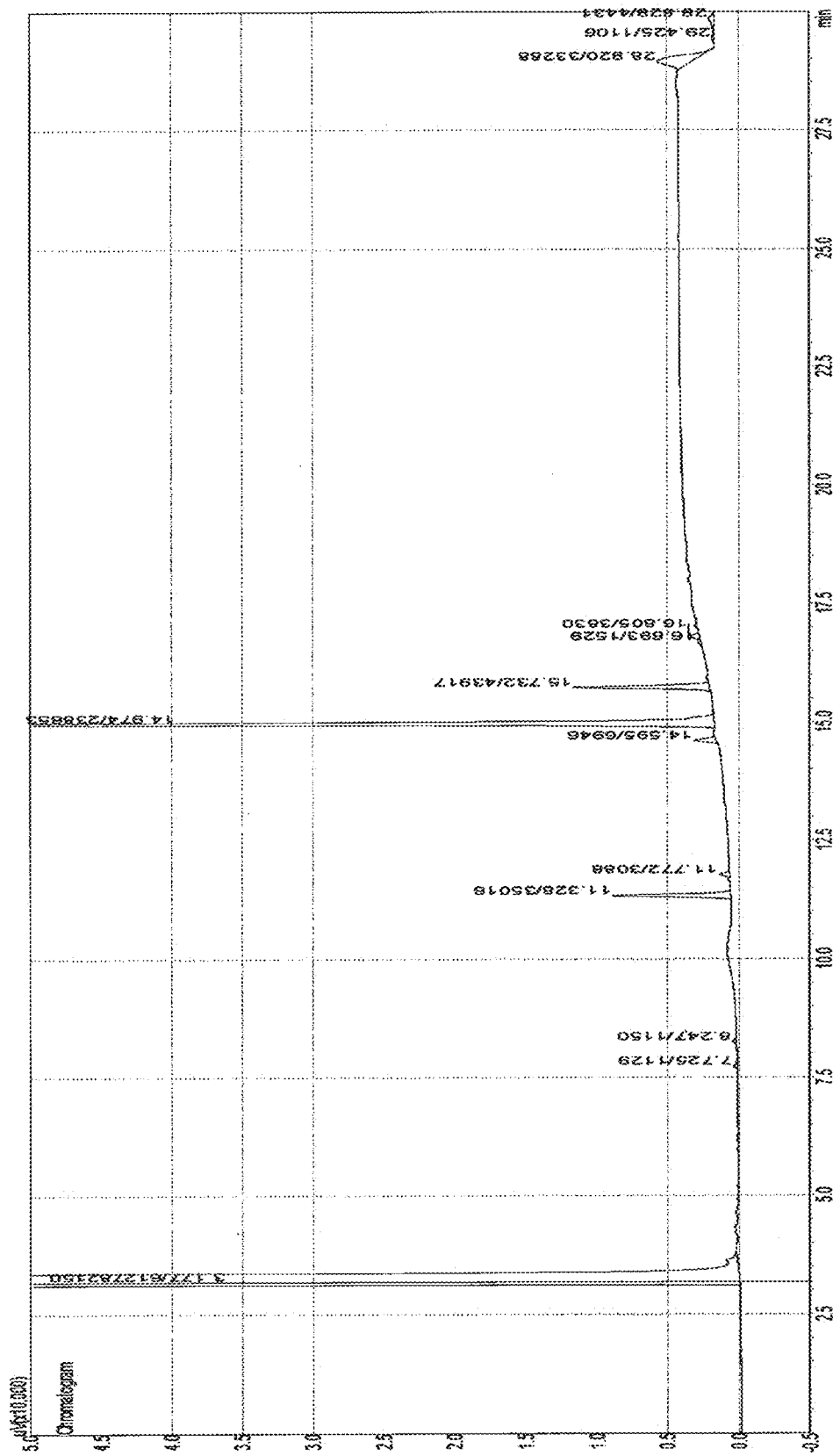

Oven temperature was raised at the rate of 10° C./min at the section of 70~120° C., and at 5° C./min at the section of 120~250° C. The results were shown in FIG. 2. FIG. 2a is a distribution chart of fatty acid, FIG. 2b is the result of analyzing fatty acid in the olive oil, FIG. 2c is the result of analyzing fatty acid in the fermented olive oil, FIG. 2c is the result of analyzing fatty acid in the green tea oil, and FIG. 2d is the result about the fermented green tea oil.

As the result of comparing the fatty acid composition of the olive oil and the fermented olive oil, it was confirmed that the content of essential fatty acid such as linoleic acid was more increased in the fermented olive oil than in the olive oil. Further, as the result of comparing the fatty acid composition of the green tea oil and the fermented green tea oil, it was confirmed that the essential fatty acid content such as linoleic acid was more increased in the fermented green tea oil than in the green tea oil.

From the above results, the fermented oil improved water retention ability and absorbing ability of the skin as the essential fatty acid content was increased. Accordingly, it was confirmed that the fermented oil is effective for improving moisture feeling.

4. Free Fatty Acid Measurement

The acid value is the amount of free fatty acid that is in unbound glyceride form. In order to check whether the first free fatty acid was changed or not, the acid value was measured by using a metrohm titrator. A sample was added in an amount to make the estimated consumption of a titrant (KOH 0.05 mol/L) is between 1 ml and 10 ml. Property of the sample was homogenized, and then a supplementary solution (methanol:distilled water=3:1) 50 ml was added thereto. MET mode of the device was selected, U (voltage) was selected among measuring values, MET U mode was loaded, an electrode and a burette tip were set in a beaker, and then the test was started. When end point was recognized, the test was finished. The same test was repeated except for not adding a sample, and the measured value was used as a blank value. Secondarily, in order to compare the free fatty acid content of each oil, the acid value was measured by Acid value test method of Food code. Oil 5-10 g was precisely weighed and added into a flask with stopper, and neutral ethanol-ether mixed solution (1:2) 100 mL was added thereto so as to dissolve the oil. The resulting solution was titrated with 0.1 N ethanolic potassium hydroxide solution until pale pink color of phenolphthalein indicator solution is kept for 30 sec.

Acid value=5.611×a×f/S

Figure 3A:
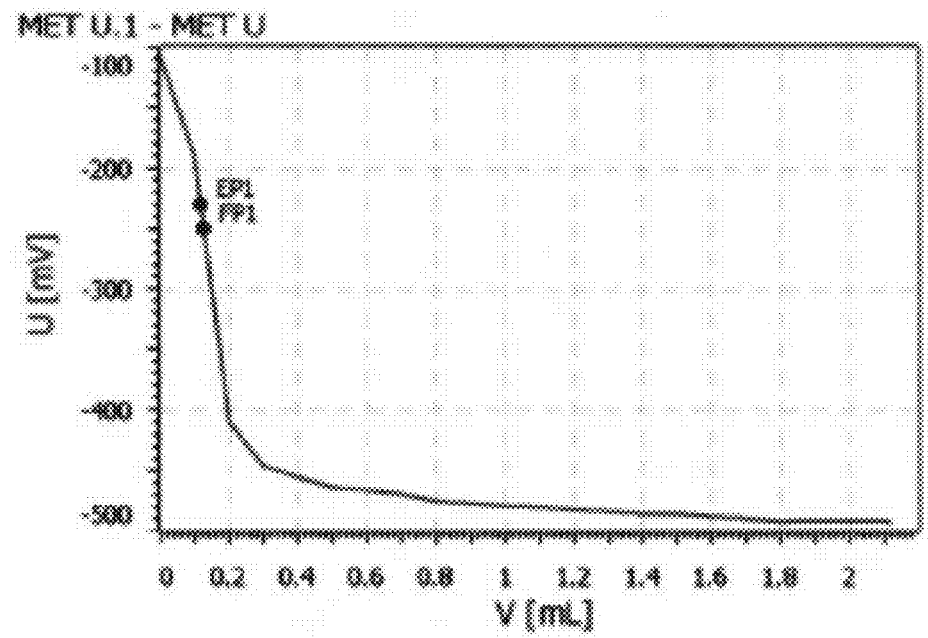
Figure 3B:
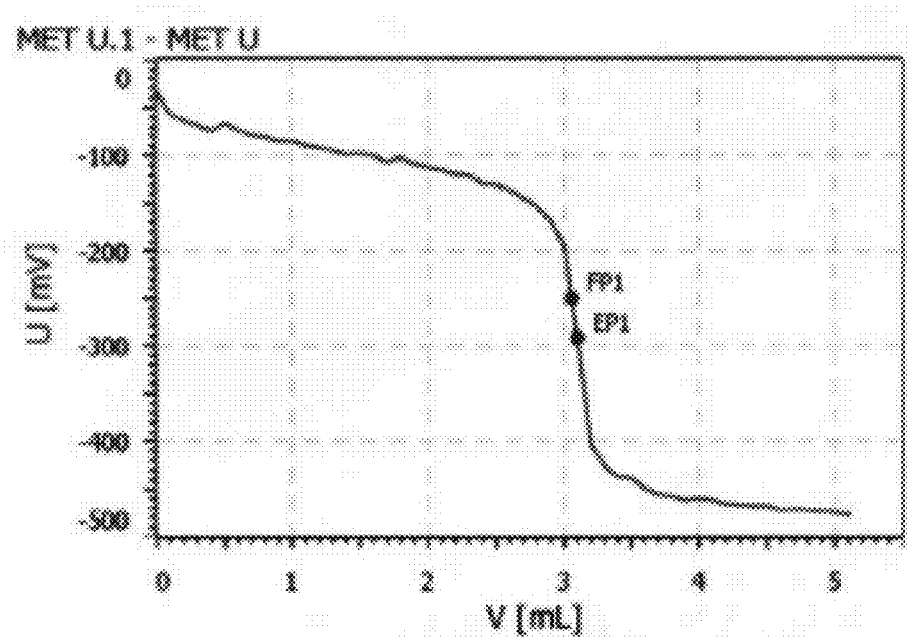
Figure 4A:
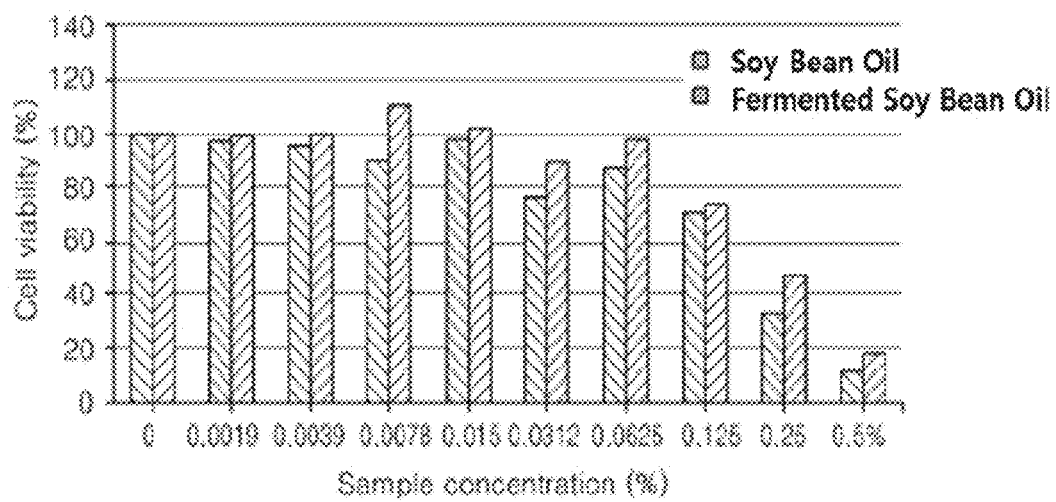
Figure 4B:
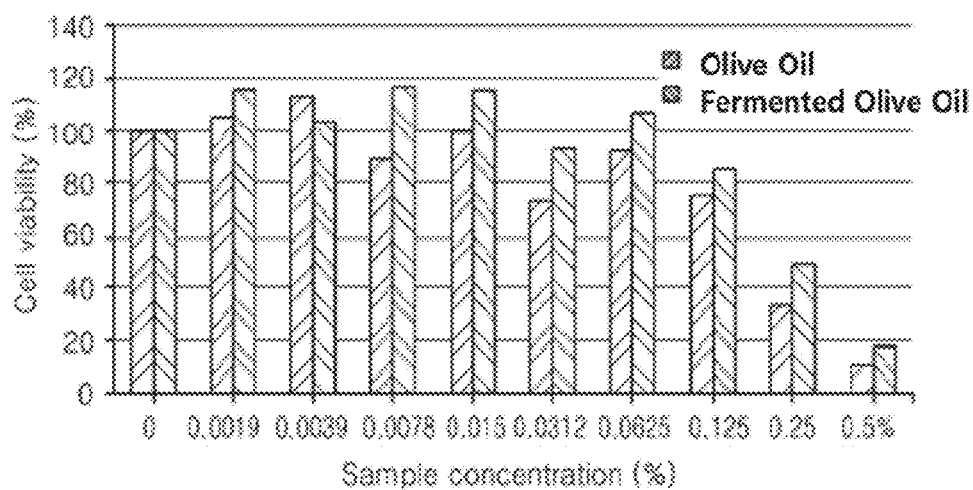
Figure 4C:
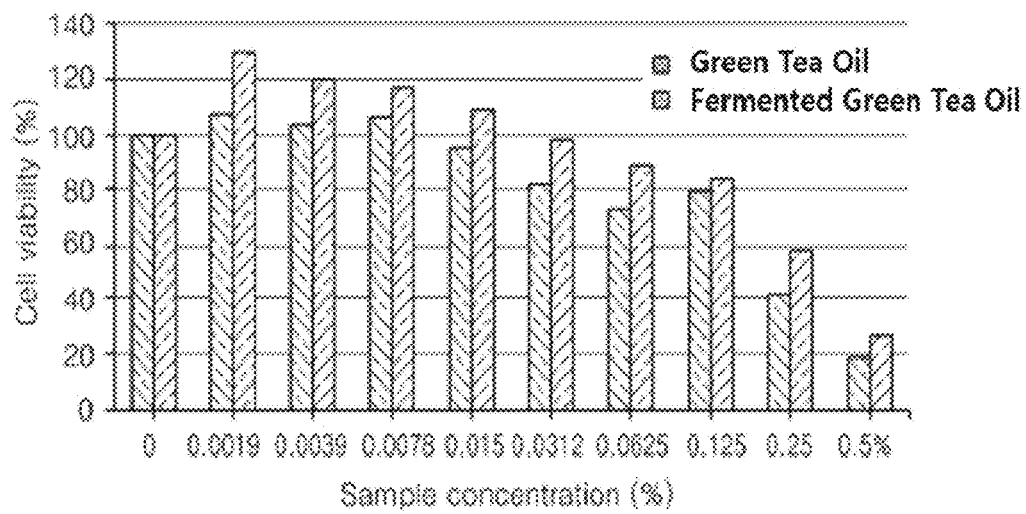
Figure 4D:
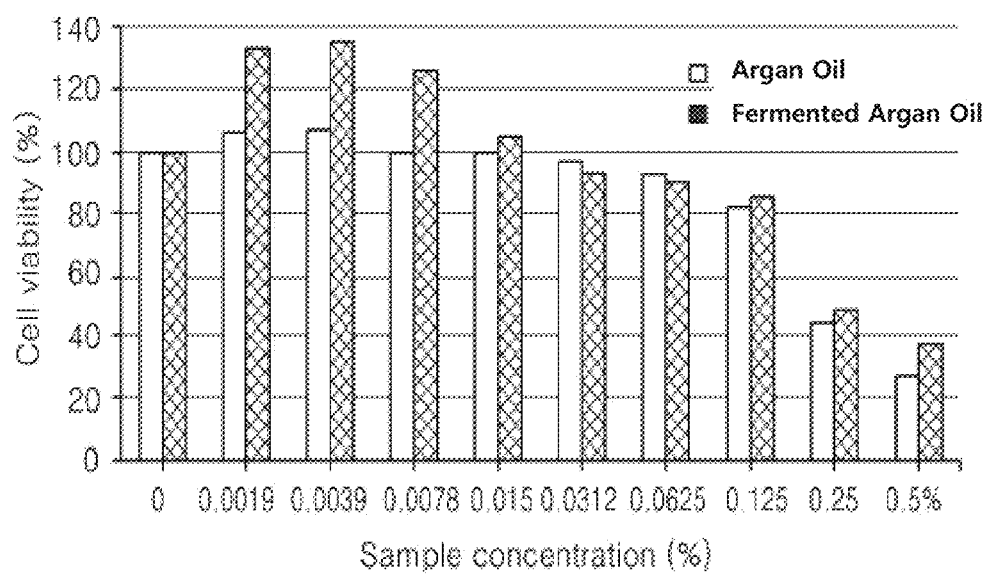

S: Sample quantity (g)
a: Consumption of 0.1 N ethanolic potassium hydroxide solution (mL)
f: Titers of 0.1 N ethanolic potassium hydroxide solution Firstly, the acid value was measured for checking whether the free fatty acid was changed during oil fermentation or not, and the results were shown in FIG. 3. FIG. 3a is the acid value of the olive oil, and FIG. 3b is the acid value of the fermented olive oil.

As the result of measuring the acid values of the olive oil and the fermented olive oil, the acid value of the olive oil was 0.1294 mgKOH/g and that of the fermented olive oil was 8.1022 mgKOH/g. Accordingly, it was confirmed that the amount of the free fatty acid of the fermented olive oil was increased 50 times or higher than that of the olive oil.

Secondarily, the acid value was measured for comparing the free fatty acid content of each oil, and the result was listed in the following Table 7.

TABLE 7

|  | Before fermentation (mg KOH/g) | After fermentation (mg KOH/g) |
|---|---|---|
| Soy bean oil | 0.57 | 33.51 |
| Olive oil | 0.35 | 39.54 |
| Green tea oil | 0.45 | 35.59 |
| Argan oil | 0.36 | 51.40 |

As the result, the contents of free fatty acid in all oils were increased about 50~140 times or more than before fermentation.

From the above results, the free fatty acid content in a general oil was increased through fermentation in an optimized medium. Accordingly, it was confirmed that texture will be improved due to reduced stickiness, and it will be effective for improving oiliness after use.

5. Test for Verifying Effect for Growing Human Dermal Fibroblast Neonatal

The olive oil and the fermented olive oil were treated to the cultured human fibroblast at various concentrations, and then cell viabilities were compared for verifying influence of the fermentation process on the cell growth and toxicity.

MTT is absorbed into cells, and forms formazan in mitochondria by succinic acid dehydrogenase. Intracellular accumulation of the formazan means the activity of mitochondria, broadly, the cell activity. Accordingly, the cell growth and toxicity can be tested.

Olive oil and fermented olive oil were treated to cells cultured in a 96 well plate at the concentration of 0.5%~0.0019%, respectively, and then cultured for 48 hours in a 5% CO2, 37° C. incubator. The cells were reacted in MTT solution for 3-4 hours, and then O.D value was measured at 540 nm by ELISA analyzer. The cell viability may be calculated by the following formula.

Cell viability (%)=(O.D of group wherein sample was added at 540 nm)/O.D of group wherein sample was not added at 540 nm)×100.

DMSO-treated group was used as a control group, and the results of tests conducted by adding soy bean oil, green tea oil and argan oil before fermentation, and soy bean oil, green tea oil and argan oil after fermentation were shown in FIG. 4.

As the result, when comparing cell viabilities of the groups treated with fermented oils and the groups treated with oils not fermented, cell viabilities of the group treated with fermented oils were higher. From the above results, it was confirmed that the oils have no influence on the cell growth and toxicity even after fermentation.

6. TLC (Thin Layer Chromatography) Analysis

Ingredients contained in an olive oil and a fermented olive oil were analyzed by using TLC (Thin layer chromatography), and whether each ingredient exists or not and the degree of change were checked with the naked eye.

An olive oil and a fermented olive oil as a sample were diluted to a certain concentration (1/10, 1/5). 2-3 drops of each sample were dropped on Silica TLC, and analyzed at solvent condition having good resolution to find the optimum solvent condition. The TLC with the sample was developed with a solvent having good resolution as a developing solvent in a chamber. The developed TLC was picked out and dried. The TLC was dipped in 10% sulfuric acid for 3-4 sec, picked out again, and then dried well. The well dried TLC was heated with a drier or on a hot plate until color was developed.

Figure 5A:
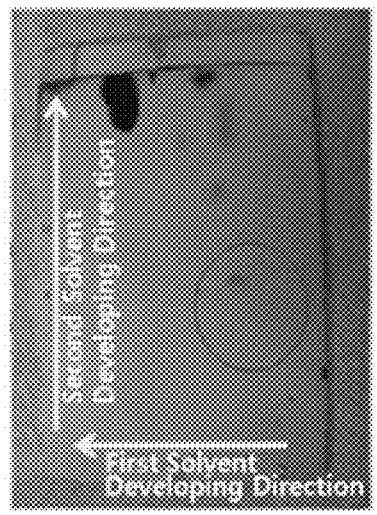

By using TLC, n-hexane:Ethyl acetate=5:1, Chloroform:Methanol=15:1 conditions, which show good resolution for olive oil and fermented olive oil were established. 2D-TLC was conducted by developing the TLC at the first solvent condition, n-hexane:Ethyl acetate=5:1, and at the second solvent condition, Chloroform:Methanol=15:1, and the result was shown in FIG. 5a.

As the result of analysis, it was confirmed that, unlike in the olive oil, certain spots became noticeably deeper and new spots were formed in the fermented olive oil. And, when comparing certain spots of the fermented olive oil with the 2D-TLCs of linoleic acid and linolenic acid, it was confirmed that the spot at the same position with linoleic acid and linolenic acid became deeper gradually. From the above results, unlike in the olive oil, the amount of very nonpolar oil was reduced, and the amounts of linoleic acid and linolenic acid were increased with time in the fermented olive oil.

Figure 5B:
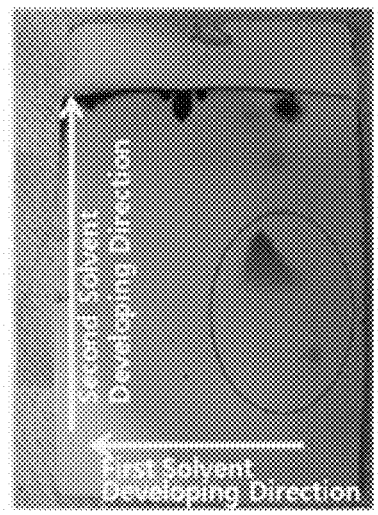
Figure 5C:
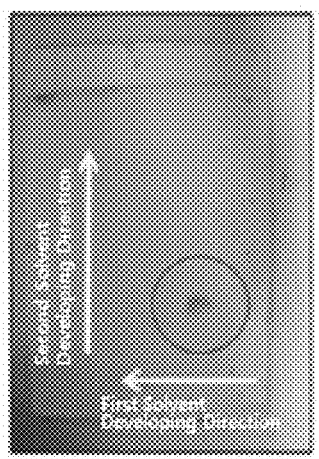
Figure 5D:
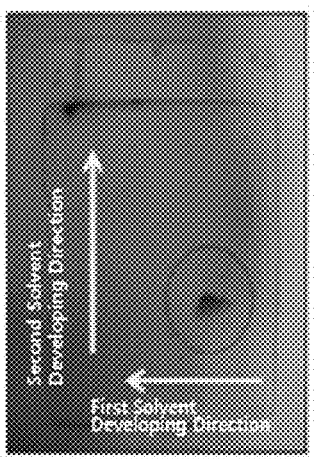
Figure 5E:
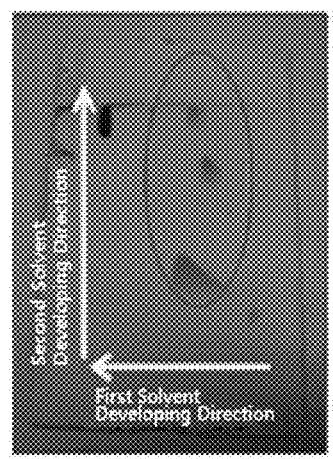
Figure 5F:
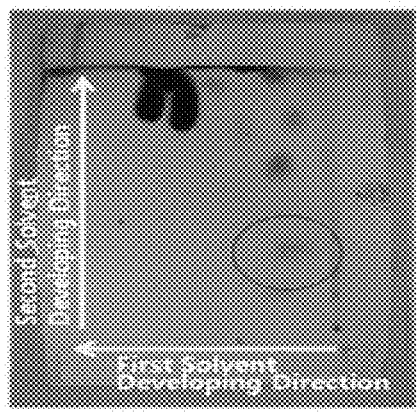
Figure 5G:
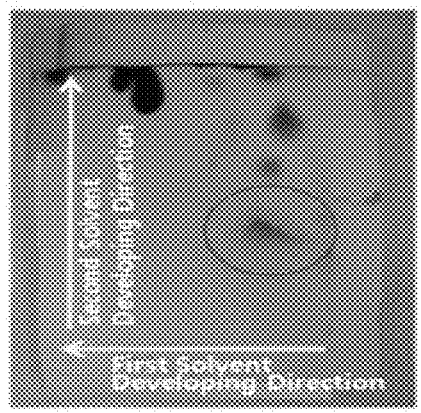
Figure 5H:
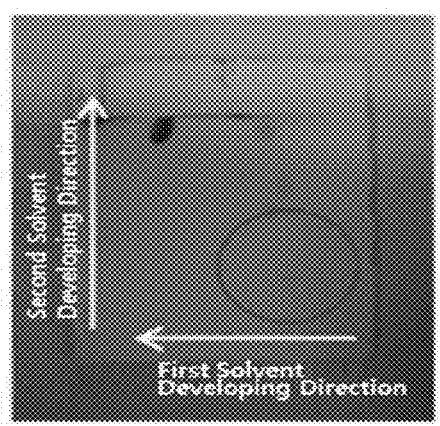
Figure 5I:
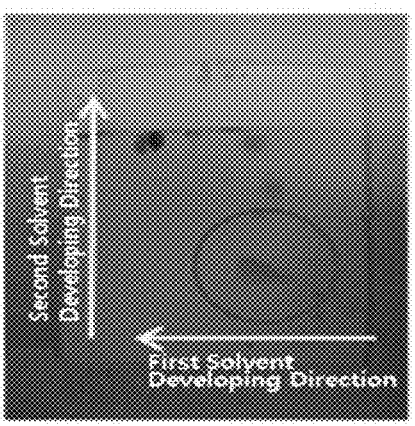
Figure 5J:
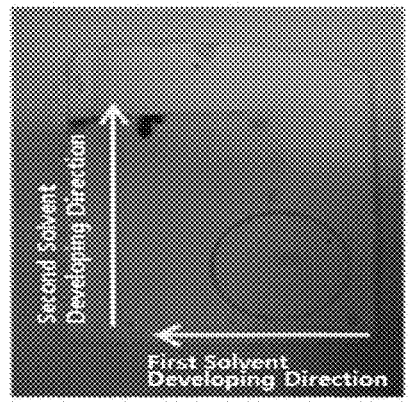
Figure 5K:
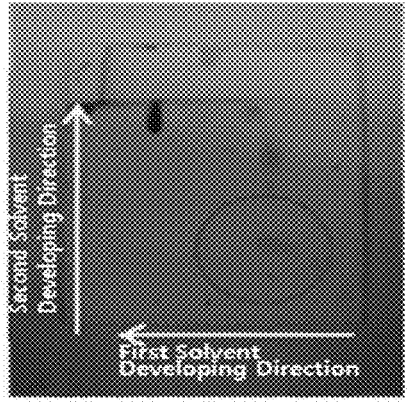

2D-TLCs of soy bean oil, green tea oil and argan oil before and after fermentation were conducted, and the result was shown in FIG. 5b.

As the result of analysis, unlike before fermentation, the amount of very nonpolar oil was reduced, and the amounts of linoleic acid and linolenic acid were increased with time also in the fermented soy bean oil, green tea oil and argan oil.

7. Formulation Example (1) Formulation Example 1: External Cream Formulation

An external cream formulation was formulated with the composition of the following Table 8. First of all, a moisturizer was added to purified water, and the resulting solution was heated and adjusted to 70° C. to form aqueous phase. A fermented olive oil and other oil ingredients were heated and dissolved, and an emulsifier, a preservative and the like were then added thereto and the temperature was adjusted to 70° C. The resulting solution was added to the above aqueous phase and emulsified particles were homogenized with a homomixer, and then deaeration, filtration, and cooling were performed.

TABLE 8

| Medium scale | Small scale | Content (%) |
|---|---|---|
| Oil | Cetostearyl alcohol | 6.0 |
| | Stearic acid | 2.0 |
| | Fermented olive oil | 15.0 |
| | Squalane | 1.0 |
| | Octyldodecanol | 3.0 |
| Emulsifier | POE(25) cetylalcohol ether | 3.0 |
| | Glyceryl monostearate | 2.0 |
| Moisturizer | 1,3-butyleneglycol | 3.0 |
| | Glycerin | 2.0 |
| Preservative | 1,2-hexyleneglycol | 2.0 |
| Purified water | — | 61.0 |

(2) Formulation Example 2: External Lotion Formulation

An external lotion formulation was formulated with the composition of the following Table 9. First of all, a moisturizer was added to purified water, and the resulting solution was heated and adjusted to 70° C. to form aqueous phase. A fermented olive oil and other oil ingredients were heated and dissolved, and an emulsifier, a preservative and the like were then added thereto and the temperature was adjusted to 70° C. The resulting solution was added to the above aqueous phase and homogenized with a homomixer, hyaluronic acid aqueous solution was added thereto and homogeneously mixed with a homomixer, and then deaeration, filtration, and cooling were performed.

TABLE 9

| Medium scale | Small scale | Content (%) |
|---|---|---|
| Oil | Cetostearyl alcohol | 1.0 |
| | Fermented olive oil | 8.0 |
| | Squalane | 1.0 |
| | Dimethyl polysiloxane | 2.0 |
| Emulsifier | POE(25) cetylalcohol ether | 1.0 |
| | Glycerol monostearate ester | 1.0 |
| Moisturizer | 1,3-butyleneglycol | 4.0 |
| | Glycerin | 4.0 |
| Preservative | 1,2-hexyleneglycol | 2.0 |
| Purified water | — | 76.0 |

While the invention has been described with respect to the above specific embodiments, it should be recognized that various modifications and changes may be made and also fall within the scope of the invention. Therefore, it should be understood that the scope of the present invention cannot be limited by the above described specific embodiments in any way.

What is claimed is:

1. A method for preparing a fermented vegetable oil, the method comprising:
   (a) culturing a yeast in a culture solution at an aerobic condition to form a cultured yeast solution;
   (b) adding a vegetable oil to the cultured yeast solution to form a cultured vegetable oil; and
   (c) further culturing the yeast in the cultured vegetable oil to ferment the vegetable oil; and
   (d) collecting the fermented vegetable oil from the cultured vegetable oil,
   wherein the yeast is *Pseudozyma* SY16, KCTC 8950P,
   wherein the free fatty acid content of the fermented vegetable oil formed in step (c) is greater than the free fatty acid content of the vegetable oil added in step (b), and
   wherein the culture solution comprises 3 g/l soya bean meal and 0.1 g/l NaCl per liter of the culture solution.

2. The method of claim 1, wherein the acid value of the vegetable oil added in step (b) is 0.100-2.000.

3. The method of claim 1, wherein step (a) is conducted for 36-60 hours.

4. The method of claim 1, wherein the fermented vegetable oil has an essential fatty acid content greater than an essential fatty acid content of the vegetable oil added in step (b), wherein
   the essential fatty acid content of the fermented vegetable oil is composed of linoleic acid, linolenic acid or a combination thereof, and
   the essential fatty acid content of the vegetable oil added in step (b) is composed of linoleic acid, linolenic acid or a combination thereof.

5. The method of claim 4, wherein the essential fatty acid content of the fermented vegetable oil is 5-140 times greater than the vegetable oil added in step (b).

6. The method of claim 1, wherein the free fatty acid content of the fermented vegetable oil is 5-140 times greater than the vegetable oil added in step (b).

7. The method of claim 1, wherein step (c) is conducted for 72-120 hours.

8. The method of claim 1, wherein the vegetable oil is olive oil.

9. The method of claim 1, wherein the vegetable oil is green tea oil.

10. The method of claim 1, wherein the vegetable oil is soy bean oil.

11. The method of claim 1, wherein the vegetable oil is argan oil.

12. The method of claim 1, wherein the vegetable oil is grape seed oil.

13. The method of claim 1, wherein the vegetable oil is meadowfoam seed oil.

14. The method of claim 1, wherein the culture solution further comprises:
   water;
   a vegetable oil;
   glucose;
   yeast extract;
   malt extract;
   peptone;
   $(NH_4)_2SO_4$;
   $KH_2PO_4$;
   $MgSO_4$; and
   $CaCl_2$.

15. The method of claim 14, wherein the culture solution comprises:
   100 grams of the vegetable oil;
   10 grams of glucose per liter of the culture solution;
   3 grams of yeast extract per liter of the culture solution;
   3 grams of malt extract per liter of the culture solution;
   3 grams of peptone per liter of the culture solution;
   2 grams of $(NH_4)_2SO_4$ per liter of the culture solution;
   1 gram of $KH_2PO_4$ per liter of the culture solution;
   0.5 grams of $MgSO_4$ per liter of the culture solution; and
   0.1 grams of $CaCl_2$ per liter of the culture solution.

16. The method of claim 14, wherein the vegetable oil is selected from the group consisting of olive oil, green tea oil, soy bean oil, argan oil, grape seed oil, and meadowfoam seed oil.

17. The method of claim 1, wherein the culture solution further comprises:
malt extract; and
$(NH_4)_2SO_4$.

18. The method of claim 1, wherein the culture solution further comprises:
malt extract.

* * * * *